United States Patent [19]

Smith

[11] Patent Number: 5,654,176
[45] Date of Patent: Aug. 5, 1997

[54] FUSION PROTEINS CONTAINING GLUTATHIONE-S-TRANSFERASE

[75] Inventor: Donald Bruce Smith, Berwickshire, Scotland

[73] Assignee: Amrad Corporation Limited, Victoria, Australia

[21] Appl. No.: 307,337

[22] Filed: Sep. 16, 1994

Related U.S. Application Data

[63] Continuation of Ser. No. 865,718, Apr. 8, 1992, abandoned, which is a continuation of Ser. No. 331,521, filed as PCT/AU88/00164, May 27, 1988 published as WO88/09372, Dec. 1, 1988, abandoned.

[30] Foreign Application Priority Data

May 28, 1987 [AU] Australia ................. PI2195/87

[51] Int. Cl.$^6$ ............... C12P 21/00; C12N 5/10; C12N 15/62; C12N 15/63
[52] U.S. Cl. ............ 435/69.7; 435/193; 435/252.3; 435/252.33; 435/320.1; 435/348; 530/350; 536/23.4
[58] Field of Search ............... 435/69.7, 172.3, 435/320.1, 252.3, 69.1, 240.2, 252.33; 536/23.4; 530/350, 300

[56] References Cited

U.S. PATENT DOCUMENTS

| | | | |
|---|---|---|---|
| 4,751,180 | 6/1988 | Cousens et al. | 435/69.7 |
| 4,760,023 | 7/1988 | Miyoshi et al. | 435/252.33 |
| 4,769,326 | 9/1988 | Rutter | 435/68.1 |
| 4,797,474 | 1/1989 | Patroni et al. | 530/351 |
| 4,894,436 | 1/1990 | Auerswald et al. | 530/324 |

OTHER PUBLICATIONS

Smith, et al.; Single–step purification of polypeptides expressed in *E. coli* as fusions with glutathione S–transferase; Gene, 67:31–40 (1988).

Young, et al.; Efficient isolation of genes by using antibody probes; PNAS, 80:1194–98 (1983).

Gray, et al.; Open reading frame cloning:Identification, cloning and expression of open reading frame DNA; PNAS, 79:6598–6602 (1982).

Stanley, et al.; Construction of a new family of high efficiency bacterial expression vectors: identification of cDNA clones for human liver proteins; EMBO Journal, 3(6):1429–1434 (1984).

Ruther, et al.; Easy identification of cDNA clones; EMBO Journal, 2(10):1791–1794 (1983).

Expression in *E. coli* of a chemically synthesized gene for the hormone somatostatin; Science; 198:1056–1063 (1977).

Nagai, et al.; Generation of beta–globin by sequence-specific proteolysis of a hybrid protein produced in *E. coli* Nature, 309:810–812 (1984).

Koenen, et al.; Immunoenzymatic detection of expressed gene fragment cloned in the lac Z gene of *E. coli*; EMBO Journal, 1(4):509–512 (1982).

Ullmann, Agnes; One-step purification of hybrid protein which have beta–galactosidase activity; Gene, 29:27–31 (1984).

Germino, et al.; Use of gene fusions and protein–protein interaction in the isolation of a biologically active . . . plasmid R6K; PNAS, 80:6848–6852 (1983).

(List continued on next page.)

*Primary Examiner*—Charles L. Patterson, Jr.
*Assistant Examiner*—Eric Grimes
*Attorney, Agent, or Firm*—Scully, Scott, Murphy & Presser

[57] ABSTRACT

A recombinant DNA molecule comprising a nucleotide sequence which codes for expression of a fusion protein in which a foreign protein or peptide is fused with the enzyme glutathione-S-transferase, is disclosed, as well as expression vectors or host cells containing such a molecule. Optionally, the foreign protein or peptide is fused to the enzyme through a cleavable link. Also disclosed is an expression vector having inserted therein a nucleotide sequence capable of being expressed as the enzyme glutathione-S-transferase followed by at least one restriction endonuclease recognition site for insertion of a nucleotide sequence capable of being expressed as a foreign protein or peptide fused to the glutathione-S-transferase.

25 Claims, 9 Drawing Sheets

OTHER PUBLICATIONS

Germino, et al.; Rapid purification of a cloned gene product by genetic fusion and site-specific proteolysis; PNAS, 81:4692–4696 (1984).

Collins et al.; Immunization of Aotus monkeys with recombinant proteins of an erythrocyte surface antigen of Plasmodium falciparum; Nature, 323:259–262 (1986).

Pharmacia LKB Biotechnology; GST gene fusion system chimeric proteins–versatile tools in molecular biology research; Analects, 19(3):1–8 (1991).

Coppel, et al.; Isolate-specific S-antigen of Plasmodium falciparum contains a repeated sequence of eleven amino acids; Nature, 306:751–756 (1983).

Martson, Fiona; The purification of eukaryotic polypeptides synthesized in E. coli; Biochem., 240:1–12 (1986).

Sassenfeld, Helmut; Engineering proteins for purification; Tibtech, 8:88–93 (1990).

Lew, et al.; Recombinant fusion proteins of protein A and protein G with glutathione S-transferase as reporter molecules; J. Immunol. Methods, 136:211–219 (1991).

Frorath, et al.; Cloning and expression of antigenic epitopes of the human 68–kDa (U1) ribonuycleoprotein antigen in E. coli; BioTechniques, 11(3):364–371 (1991).

Sipos, et al.; Cloning and sequencing of the genes coding for the 10– and 60–kDa heat shock proteins from Pseudomonas aeruginosa and mapping of a species-specific epitope; Infect. Immun., 59(9):3219–26 (1991).

Ausubel, et al.; Current protocols in molecular biology; Wiley & Sons; 1:Unit 16.4.1–16.7.8 (1990).

Johnson, et al.; Vaccination against ovine cysticercosis using a defined recombinant antigen; Nature, 338:585–587 (1989).

Kalinyak et al. J. Biol. Chem 257:523 (1982).

Manoharan J Biol Chem 262:3739 (1987).

Haber et al. Fed Proc. Dec. 1983 42(15):3155 (abstract).

Smith et al. PNAS 83:8703 (1986).

Simons et al. Anal. Biochem. 82(2):334 (1977) (abstract).

Pierce et al. Mem. Inst. Oswaldo. Cruz. 82(4):111 (1987) (abstract).

Balloul et al. Nature 326:149 (1987).

Pickett et al. J. Biol. Chem. 259:5182 (1984).

Telakoski-Hopkins J. Biol Chem 260(1985):5820.

Ding et al. J Biol Chem 260:13268 (1985).

Tu et al. Nuc Acid Res 10:5407 (1984).

Pro Lys Ser Asp Pro Arg Glu Phe Ile Val Thr Asp ***
CCA AAA TCG GAT CCC CGG GAA TTC ATC GTG ACT GAC TGA CGA TCT G
         BamHI  SmaI   EcoRI

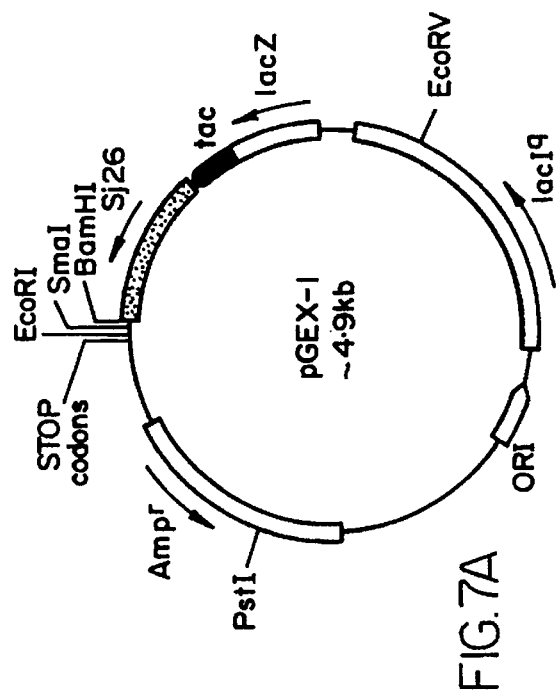

FIG. 7A

```
              Pro Lys Ser Asp Pro Arg Glu Phe Ile Val Thr Asp ***
pGEX-1        CCA AAA TCG GAT CCC CGG GAA TTC ATC GTG ACT GAC TGA  CGA TCT G
                          └────────────────┘
                           BamHI  SmaI  EcoRI
                                   Thrombin
              Pro Lys Ser Asp Leu Val Pro Arg│Gly Ser Pro Gly Ile His Arg Asp ***
pGEX-2T       CCA AAA TCG GAT CTG GTT CCG CGT GGA TCC CCG GGA ATT CAT CGT GAC TGA  CTG ACG ATC TG
                                             └────────────────┘
                                              BamHI  SmaI  EcoRI
                     Factor X
              Pro Lys Ser Asp Leu Ile Glu Gly Arg│Gly Ile Pro Gly Asn Ser Ser ***
pGEX-3X       CCA AAA TCG GAT CTG ATC GAA GGT CGT GGG ATC CCC GGG AAT TCA TCG TGA  CTG ACT GAC GAT CTG
                                                 └────────────────┘
                                                  BamHI  SmaI  EcoRI
```

FIG. 7B

FUSION PROTEINS CONTAINING GLUTATHIONE-S-TRANSFERASE

This is a continuation of application(s) Ser. No. 07/865,718 filed on Apr. 8, 1992 now abandoned, which is a continuation of U.S. Ser. No. 07/331,521 filed Feb. 7, 1989 now abandoned, corresponding to International Application PCT/AU88/00164 filed on May 27, 1988 published as WO88/09372, Dec. 1, 1988 and which designated the U.S.

BACKGROUND OF THE INVENTION

This invention relates to the cloning and expression of foreign proteins and polypeptides in bacteria such as *Escherichia coli*. In particular, this invention relates to the expression of bacterially synthesised foreign proteins or polypeptides as fused polypeptides which are in general soluble and which can be readily purified from bacterial lysates without altering the antigenicity or destroying the functional activity of the foreign protein or polypeptide.

A number of different vectors have been described that direct the expression of foreign polypeptides in *Escherichia coli* (reviewed by Harris, 1983; Marston, 1986; McIntyre et. al., 1987). Some vectors have been designed to simplify product purification but a difficulty common to most of these systems is that denaturing reagents are required to maintain the solubility of proteins or to elute them from affinity reagents. Denaturation may be expected to alter the antigenicity and destroy any functional activity of the foreign polypeptide. For example, polypeptides expressed as $NH_2$-terminal or COOH-terminal fusions with *E. coli* β-galactosidase (Gray et. al., 1982; Koenen et. al., 1982; Ruther & Muller-Hill, 1983) and that are soluble in 1.6M NaCl, 10 mM β-mercaptoethanol can be purified from crude cell lysates by affinity chromatography on a column of p-aminophenyl-β-D-thiogalactoside followed by elution in 0.1M sodium borate pH 10, 10 mM β-mercaptoethanol (Germino et. al., 1983; Ullmann, 1984). Such fusion proteins will also bind to immobilised anti-β-galactosidase antibodies and can be recovered by elution in solutions of high or low pH (Promega biotec). Alternatively, fusions with β-galactosidase that lack the last 16 COOH-terminal amino acids of β-galactosidase are frequently insoluble (Itakura et. al., 1977; Young & Davis, 1983; Stanley & Luzio, 1984) and so can be purified from the insoluble fraction of lysed bacteria after resolubilisation by treatment with denaturing reagents (Marston, 1986). The same method can be used to purify polypeptides expressed as insoluble COOH-terminal fusions with a protein containing the trpE leader sequence and the COOH-terminal third of the trpE protein (Kleid et. al., 1981). Apart from the use of denaturing conditions, these methods suffer from the disadvantage that the *E. coli* proteins used as carriers may dominate an immune response to the fusion protein, particularly in the case of fusions with β-galactosidase (Mr 116,000), and may elicit antibodies that show undesirable cross-reactions.

Other expression vectors direct the synthesis of polypeptides as fusions with the COOH-terminus of staphyloccocal protein A that can be purified from cell lysates by affinity chromatography on a column of human IgG-Sepharose (Uhlen et. al., 1983; Nilsson et. al., 1985; Abrahmsen et. al., 1986; Lowenadler et. al., 1986). Because of the high affinity of protein A for IgG, denaturing conditions are usually required for the elution of fusion proteins although alternative strategies can be employed such as competition with excess native protein A, the use of sheep IgG which has a lower affinity for protein A (Nilsson et. al., 1985) or reduction in the size of the protein A carrier such that its affinity for IgG is reduced (Abrahmsen et. al., 1986). A more serious difficulty is that the binding of fusion proteins to IgG complicates the immunological screening of clones or analysis of recombinant products since antibodies that bind to protein A will recognise every fusion protein, regardless of their other specificities.

Another strategy for the purification of foreign polypeptides from *E. coli* is to produce polypeptides that contain poly-arginine at their COOH-terminus (Sassenfeld & Brewer, 1984). The strongly basic arginine residues increase the affinity of fusion proteins for anionic resins so that fusions can be purified by cation exchange chromatography, following which the COOH-terminal arginine residues can be removed by treatment with carboxypeptidase B. Other vectors direct the secretion of polypeptides into the periplasmic space or into the culture medium and although levels of expression are often low, secreted polypeptides are protected from degradation by bacterial proteases and separated from most other proteins (Marston, 1986; Abrahmsen et. al., 1986; Lowenadler et. al., 1986; Kato et. al., 1987). These last approaches have been used successfully in some instances, but their generality is unclear, particularly for polypeptides containing many acidic residues or that are largely hydrophobic.

SUMMARY OF THE INVENTION

According to one aspect of the present invention, there is provided a recombinant DNA molecule comprising a nucleotide sequence which codes an expression for a fusion protein in which a foreign (or heterologous) protein or peptide component is fused with the enzyme glutathione-S-transferase, preferably with the COOH-terminal of the enzyme.

The novel fusion protein of the present invention having the foreign peptide component fused to the enzyme glutathione-S-transferase (E.C. 2.5.1.18) avoids several of the difficulties associated with known fusion proteins. In particular, the fusion protein of this invention is soluble and can be purified from bacterial lysates under non-denaturing conditions, for example by affinity chromatography on a column of immobilised glutathione.

In one particular embodiment of this invention described in detail herein, the enzyme is a glutathione-S-transferase of the parasite helminth *Schistosoma japonica*. The glutathione-S-transferase in the fusion protein may, however, be derived from other species including human and other mammalian glutathiane-S-transferase.

In work leading to the present invention, it has been shown that a wide variety of eukaryotic polypeptides can be expressed in *E. coli* as soluble and stable glutathione-S-transferase fusion proteins that can be readily purified under physiological conditions.

In another aspect, this invention provides an expression vector, such as a bacterial plasmid, having inserted therein the nucleotide sequence as described above. Such an expression vector will preferably also comprise an expression control sequence operatively linked to the nucleotide sequence for expression of the fusion protein. In addition, the present invention extends to a host cell containing this expression vector.

The present invention further extends to a method for production of a fusion protein, which method comprises the steps of culturing a host cell containing an expression vector as described above to provide expression of said fusion protein, and optionally recovering the fusion protein from said cell culture.

Since the fusion protein is generally soluble and readily recovered from bacterial lysates, the preferred method of recovery of the fusion protein comprises the steps of lysing the bacterial cells, and recovering the fusion protein from the bacterial lysate by contacting it with immobilised glutathione.

The fusion protein of the present invention may be used as such, since the foreign protein or peptide component thereof retains its antigenicity and functional activity. Alternatively, the fusion protein may be cleaved to provide synthetic foreign protein or peptide. If production of such synthetic foreign protein or peptide is desired, a cleavable link is preferably provided in the fusion protein between the glutathione S-transferase and the foreign (or heterologous) protein or peptide component.

Since the present invention is amenable to the expression and purification of a variety of foreign proteins or peptides, in another aspect the present invention provides an expression vector, such as a bacterial plasmid, having inserted therein a nucleotide sequence which codes an expression for the enzyme glutathione S-transferase followed by at least one restriction endonuclease recognition site for insertion of a nucleotide sequence capable of being expressed as a foreign (or heterologous) protein or peptide.

DETAILED DESCRIPTION OF THE INVENTION

In one specific illustration of the present invention, there has been constructed a series of plasmid expression vectors (pGEX) that simplify the purification of foreign polypeptides produced in $E. coli$. A plasmid that directs the synthesis of enzymatically-active Sj26 in $E. coli$ has been constructed (Smith et. al., 1987b). Many mammalian glutathione S-transferase isozymes can be purified by affinity chromatography on immobilised glutathione followed by elution through competition with excess reduced glutathione (Simons & Vander Jagt, 1977; Mannervik, 1985) and this property is shared by both native Sj26 and recombinant Sj26 produced in $E. coli$ (Smith et. al., 1986, 1987b). In accordance with the present invention, polypeptides are expressed as COOH-terminal fusions with the Mr 26,000 antigen (Sj26) encoded by the parasite helminth $Schistosoma japonicum$ as a glutathione-S-transferase and can be purified under non-denaturing conditions by affinity chromatography on immobilised glutathione. Soluble material from lysed bacteria is mixed with glutathione-agarose beads and after washing, fusion protein is eluted, for example, with 50 mM Tris-HCl (pH 8.0) containing 5 mM reduced glutathione. Using batch washing procedures, several fusion proteins can be purified in parallel in less than two hours with yields of between 1.6 and 15 mg/litre of culture. Glutathione-agarose beads have a capacity of at least 8 mg fusion protein/ml swollen beads and can either be used several times for different preparations of the same fusion protein or else recycled by washing with 3M NaCl (Simons & Vander Jagt, 1981).

This system has been successfully applied to the expression and purification of various antigens of $P. falciparum$. Of 21 different $P. falciparum$ cDNAs or cDNA fragments that have been expressed in the pGEX vectors, 14 have given rise to soluble or partially soluble fusion proteins that could be purified by affinity chromatography on immobilised glutathione.

In a minority of cases, purification has been unsuccessful and these failures are all attributable to insolubility of the fusion protein. Insolubility is a frequent characteristic of foreign proteins expressed in $E. coli$ (Harris, 1983; Marston, 1986) and in this context it is surprising that the majority of glutathione S-transferase fusion proteins are wholly or partly soluble. Little is known about the factors responsible for insolubility (Marston, 1986) but in several instances insolubility of glutathione S-transferase fusion proteins is associated with the presence of strongly hydrophobic regions and elimination of these regions greatly increases stability and/or solubility. Other insoluble fusion proteins either contain many charged residues or are larger than Mr 100,000. Insoluble fusion proteins can nevertheless be purified by affinity chromatography if they are solubilised in a solubilising agent which does not disrupt binding to glutathione-agarose, such as 1% Triton X-100, 1% Tween 20, 10 mM dithiothreitol or 0.03% $NaDodSO_4$. Purification of other insoluble fusion proteins must be by conventional methods (Marston, 1986) unless the polypeptide can be expressed in several fragments that each form a soluble fusion protein. Insolubility has sometimes been associated with increased protein stability in $E. coli$ (Cheng et. al., 1981), but not in other cases (Schoemaker et. al., 1985). Although there are some exceptions, in general both insoluble and soluble glutathione S-transferase fusion proteins are stable, and where direct comparison is possible, the stability of a polypeptide expressed as a soluble glutathione S-transferase fusion is similar to that as an insoluble β-galactosidase fusion.

Good antibody responses have been generated against the foreign polypeptide portion of fusions in immunised mice, rabbits and sheep. In particular, responses appear to be as good as or better than those to equivalent β-galactosidase fusions, perhaps reflecting the smaller size of the glutathione S-transferase carrier (Mr 26,000 compared with Mr 116, 000). Responses to Sj26 vary in different mouse strains (Davern et. al., 1987) and similar variation is observed in the response to polypeptides expressed as fusions with glutathione S-transferase.

Purified glutathione S-transferase fusion proteins appear to be good substrates for cleavage by site-specific proteases. There are few previous reports of the successful use of site-specific proteases in the cleavage of fusion proteins purified from $E. coli$ (Germino & Bastia, 1984; Nagai & Thogersen, 1984) perhaps because of denaturing reagents required to resolubilise insoluble fusion proteins inhibit proteolysis. In contrast, many glutathione S-transferase fusion proteins are soluble under conditions that are known to be optimal for proteolysis. Preferably, the protease used is one which does not cleave the glutathione S-transferase carrier and so after proteolysis the polypeptide product can be separated from the carrier and any uncleaved fusion protein by absorption with glutathione-agarose. Suitable site-specific proteases include, for example, thrombin or blood coagulation factor $X_a$ as described in detail herein, or renin (Haffey et. al., 1987).

The combination of high-level expression, frame-shifted cloning sites, rapid purification and efficient site-specific proteolysis of fusion proteins will make the pGEX vectors a powerful system for the expression of foreign polypeptides in $E. coli$. In addition to simplifying the expression and purification of polypeptides, the vectors may provide an inexpensive alternative to the chemical synthesis of peptides for use as immunogens or as immunochemical reagents. The vectors may also be convenient for the construction of cDNA libraries especially since repression of the tac promoter by the plasmid encoded $lacI^q$ allele should be efficient in $E. coli$ strains that have high transformation efficiencies, regardless of their lacI status. Transformants can be screened by conventional nucleic acid or immunochemical techniques and fusion proteins encoded by clones of interest purified by glutathione-affinity chromatography.

The novel fusion proteins of the present invention, together with the various other aspects as broadly outlined above, are illustrated by way of example only in the following Example and accompanying drawings.

BRIEF DESCRIPTION OF THE DRAWINGS

In the drawings:

FIGS. 7A and 7B shows the structure of the pGEX vectors including schematic representation of pGEX-1. The position of unique PstI and EcoRV restriction sites is indicated; and the nucleotide sequence and coding capacity of pGEX-1, pGEX-2T and pGEX-3X at the COOH-terminus of the Sj26 cDNA. The normal translation termination codon of the Sj26 cDNA began at nucleotide 7 and has been destroyed through the introduction of oligonucleotides encoding cleavage sites for BamHI, SmaI and EcoRI (underlined by brackets) and TGA stop-codons in all three frames (underlined). The vectors pGEX-2T and pGEX-3X contain additional sequences encoding protease cleavage sites recognised by thrombin and blood coagulation factor $X_a$ respectively.

(a) Timecourse of expression after induction. An overnight culture of cells transformed with pGEX-1 was diluted 1:10 in fresh medium, grown for 90 minutes and IPTG added to 1 mM. Samples were taken at the times indicated and separated by electrophoresis through a 13% NaDodSO$_4$-polyacrylamide gel followed by staining with Coomassie blue. The position and sizes (kDa) of molecular weight markers (M) are indicated.

(b) Purification of glutathione S-transferase. Cells transformed with pGEX-1 were grown as above except IPTG was added to 0.1 mM and the culture was harvested 3 hours after induction. Glutathione S-transferase was purified as described and samples taken of (T) whole cells, (P) insoluble pellet and (S) supernatant after centriguation, (U) unbound material after incubation of supernatant with glutathione-agarose beads and (E) purified material eluted from beads. Samples were equivalent to 200 μl of culture and were analysed as described above.

Figure 9:
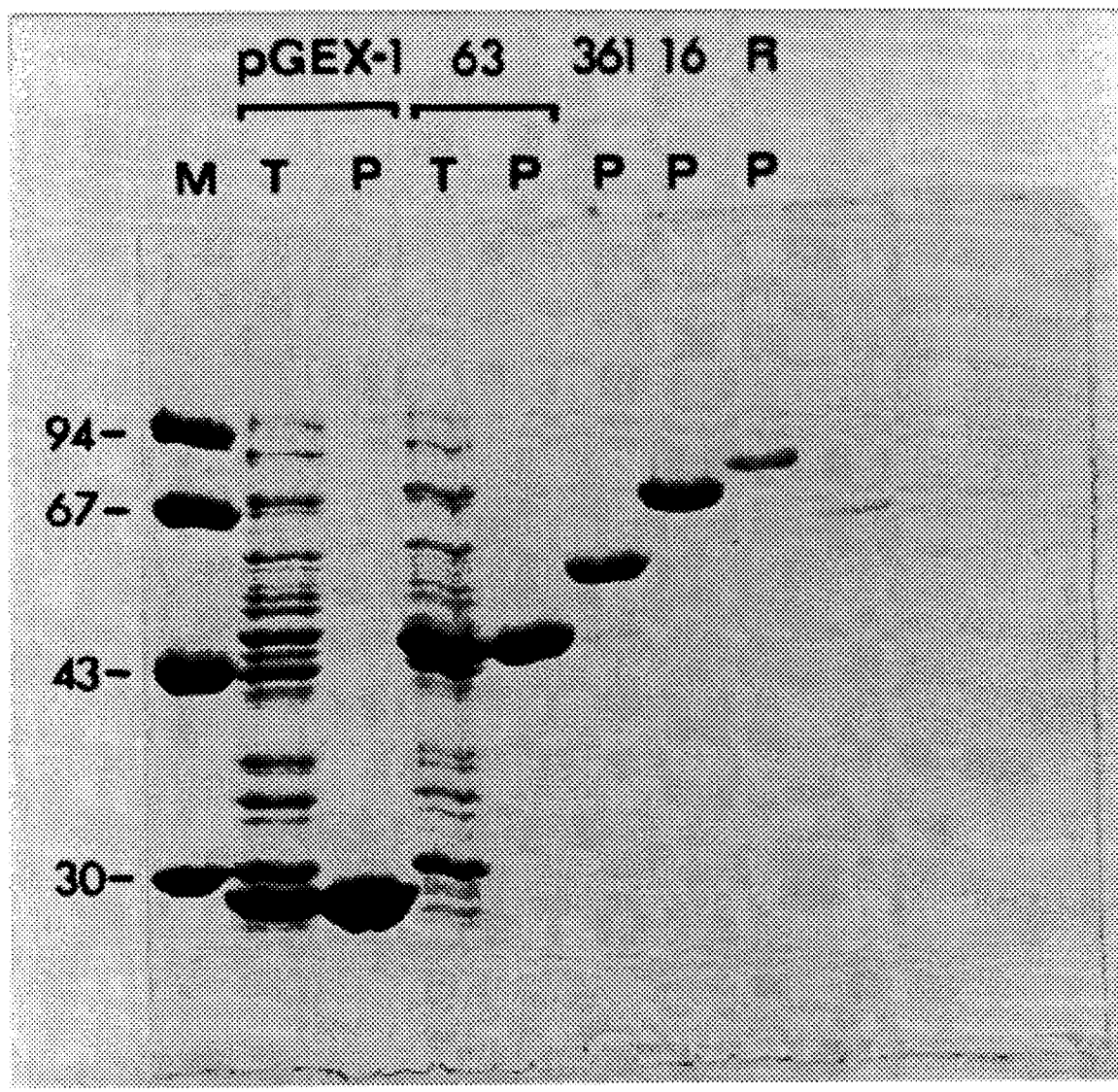

FIG. 9 shows the purification of P. falciparum antigens expressed as glutathione S-transferase fusion proteins. Samples were analysed by electrophoresis though a 10% NaDodSO$_4$-polyacrylamide gel followed by staining with Coomassie blue. (T) total cell extract, (P) material purified on glutathione-agarose. Cells were transformed with pGEX-1, Ag63 (EcoRV-EcoRI) in pGEX-3X (63), Ag361 in pSj10 (361), Ag16 in pSj10 (16) and an EcoRI fragment of RESA in pGEX-3X (R). The position and sizes (kDa) of molecular weight markers (M) are indicated.

FIG. 10 shows protease cleavage of purified fusion proteins.

(a) Thrombin cleavage. Purified fusion protein from cells transformed with pGEX-1 or with pGEX-2T containing a 580 bp RsaI-EcoRI fragment of Ag63 was incubated with protease for the number of minutes indicated. Lanes T, U & G, cleavage reactions after removal of glutathione by dilution with 40 volumes of MTPBS followed by concentration using a Centricon-10 concentrator (Amicon Corp.). (T) total reaction after concentration, (U) reaction after incubation with glutathione-agarose beads, (G) material bound to glutathione-agarose beads. Samples were analysed by electrophoresis though a 13%-NaDodSO$_4$-polyacrylamide gel followed by staining with Coomassie blue. The size (kDa) and position of molecular weight markers (M) are indicated.

(b) Blood coagulation factor $X_a$ cleavage. Purified fusion protein from cells transformed with pGEX-1 or with pGEX-3X containing a 555 bp EcoRV-EcoRI fragment of Ag63 was incubated for different periods with blood coagulation factor $X_a$ or absorbed with glutathione-agarose after cleavage and analysed as described in (a).

EXAMPLE 1

Materials and Methods

Construction of Bacterial Plasmids

Figure 1:
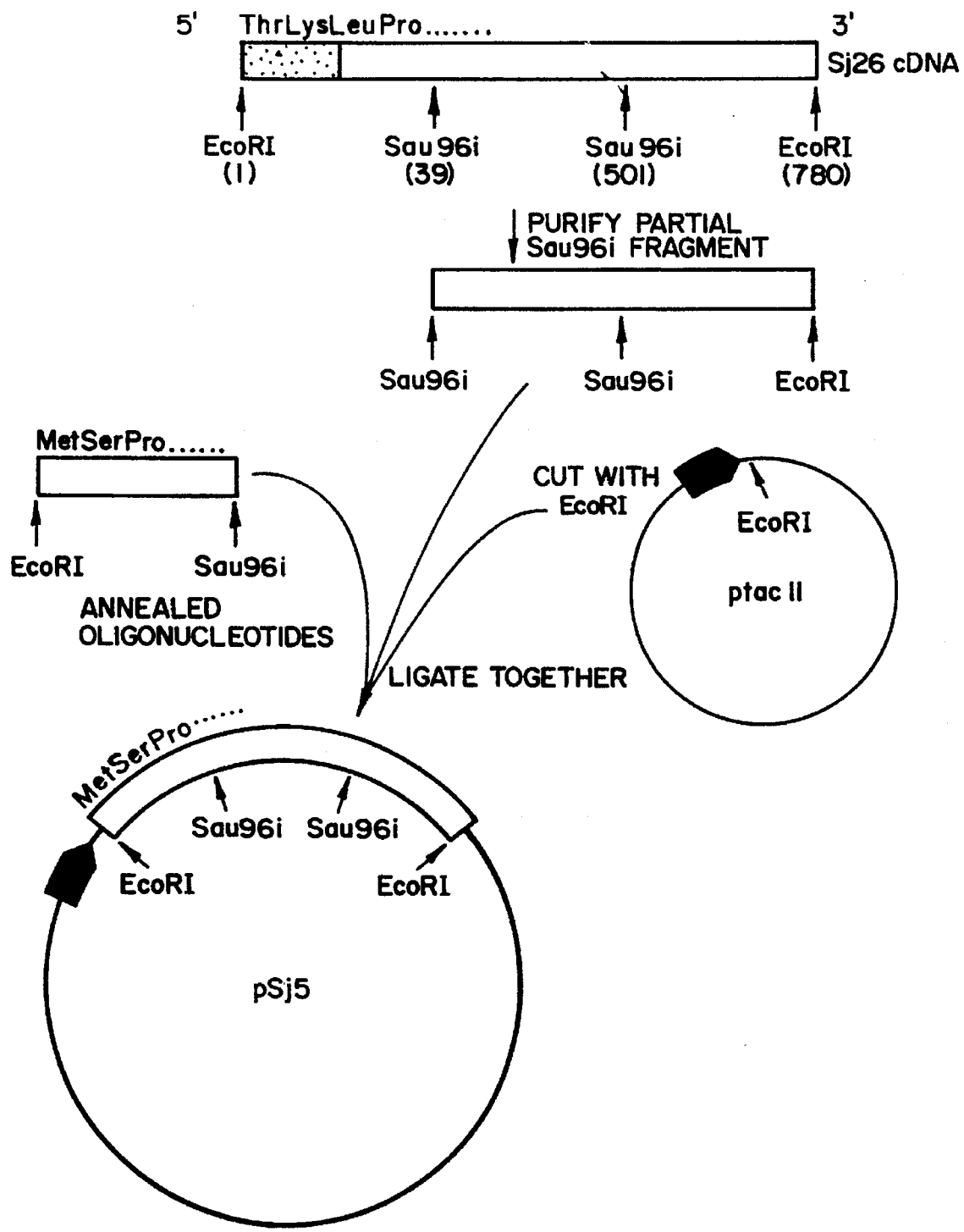
FIG. 1 outlines the scheme for the construction of the plasmid pSj5.
Figures 5A, 5B:
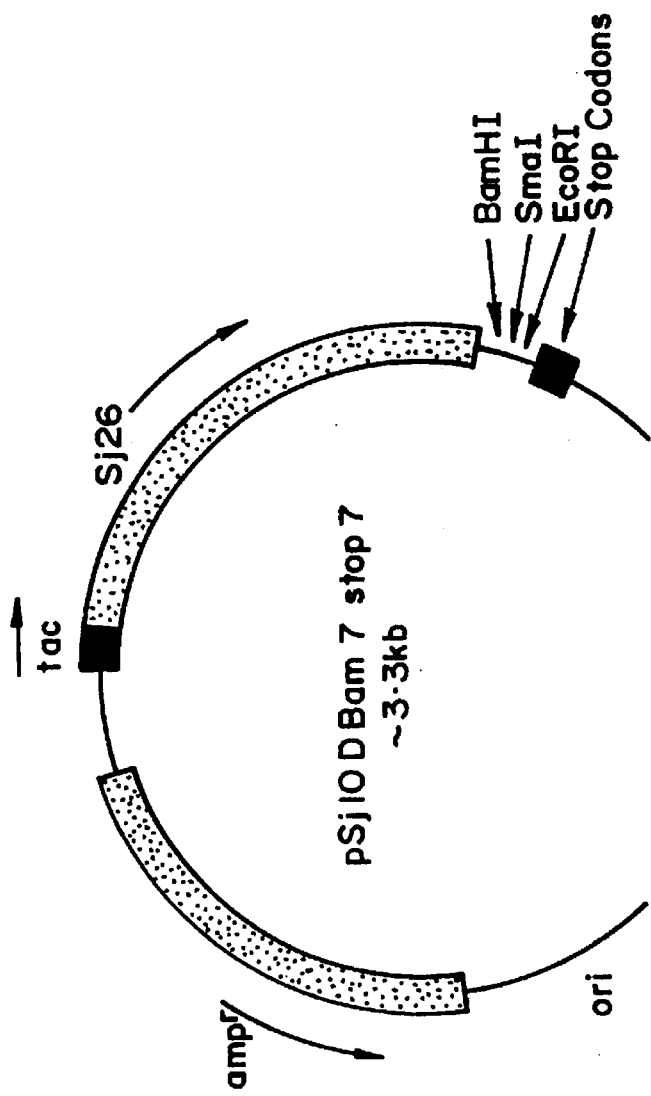
FIG. 5 shows (a) structure of pSj10DBam7Stop7 (not to scale); (b) nucleotide sequence of the last two codons of Sj26, the multiple cloning sites (underlined) into the Sj26 termination codon, the TGA termination codons in all three frames followed by the sequence of ptac12 beginning at the PvuII site (only the first three nucleotides shown, corresponding to nucleotides 2067 to 2069 of pBR322).

A 780bp EcoRI fragment of pSj1 that contains a cDNA of the Mr 26,000 Schistosoma japonicum glutathione S-transferase (Sj26) (Smith et. al., 1986) was cleaved under partial conditions with the restriction enzyme Sau96I, ligated with two annealed oligonucleotides, and inserted into the EcoRI site of ptac11 1 (Amman et. al., 1983) (FIG. 1). Upon transformation of *E. coli* JM 101 a colony was identified that contains a plasmid (pSj5) in which the tac promoter is directly followed by an EcoRI recognition site, the sequence ATGTCC (encoding Met.Ser) and then the Sj26 cDNA of pSj1 from nucleotide 12 until the 3'-terminal EcoRI site. The plasmid pSj4 was constructed in a similar fashion except that different oligonucleotides were used that introduced the sequence GATCCCACC 5' to the Met codon, the Sj26 cDNA was isolated from pSj1 as a HinfI-BamHI fragment and the reconstructed Sj26 cDNA was inserted into the BamHI site of pGS62 (Langford et. al., 1986). A BamHI fragment of pSj4 that contains the entire Sj26 cDNA was cleaved with the restriction enzyme Mn1I, ligated with BamHI linkers and cloned into the BamHI site of pLK8 (C.Langford, unpublished work), producing a plasmid (pSj7) that contains a BamHI fragment with the entire coding sequence of Sj26 up to the AAA.TAA. termination codon which has been destroyed by the introduction of a BamHI recognition site, producing the sequence AAA.TCG.GAT.CC. The Sj26 BamHI fragment was isolated from pSj7 and inserted into the BamHI site of pIC19H (Marsh et. al., 1984) producing a plasmid (pSj8) in which the 5'-terminus of Sj26 is next to the PstI recognition site. DNA from this plasmid was cleaved with the restriction enzyme PstI, incubated with 1 unit of exonuclease Ba131 (Bethesda) Research Laboratories) for 2 minutes, cleaved with EcoRV and inserted into the PvuII site of ptac12-Eco (generated from ptac12 (Amman et. al., 1983) by removal of the unique EcoRI site by treatment of EcoRI digested DNA with the Klenow fragment of *E. coli* DNA polymerase and religation). Transformants were screened for expression of Sj26 by colony immunoassay as described (Crewther et. al., 1986) using a rabbit antisera raised against whole adult worms of *S. japonicum* (Saint et. al., 1986). One strongly immuno-reactive clone (pSj10) was identified but contained two BamHI recognition sites; the BamHI site at the 5'-terminus of the Sj26 cDNA was destroyed by filling in of partially BamHI digested pSj10 DNA and religation. DNA was transformed into JM 101 (generating the plasmid pSj10DBamI) or into the methylase deficient *E. coli* strain GM48 (Yanish-Perron et. al., 1985). Plasmid DNA (pSj10DBam7) from one GM48 transformant was cleaved under partial conditions with ClaI and ligated with a pair of annealed oligonucleotides that encode TGA termination codons in all three reading frames generating the plasmid pSj10DBam7Stop7 (FIG. 5). Manipulations of DNA were performed as described (Maniatis et. al., 1982). Restriction enzymes were obtained from New England Biolabs.

Purification of Sj26-Fusion Protein

An overnight culture of bacteria was diluted 1:10 in fresh medium (800 ml), grown at 37° C. for 1 hour, induced with 0.1 mM IPTG and grown for a further 3–5 hours. Cells were collected by centrifugation, lysed by sonication in PBS and spun at 13,000 g for 10 minutes at 4° C. The supernatant was applied to a column of glutathione-agarose (Sulphur linkage) (Sigma), the column washed with PBS and the fusion protein eluted with 50 mM Tris-HCl pH 9.6 containing 5 mM reduced glutathione (Sigma) (Simons & Vander Jagt, 1977; Harvey & Beutler, 1982). Small scale purification (1.5 ml of culture) was by incubation of the supernatant of lysed cells with 50 μl of swelled glutathione-agarose beads for 30 minutes and boiling of the washed beads in protein gel sample buffer. The preparation of *S. japonicum* adult worm extract and SDS-polyacrylamide electrophoresis and immunoblotting were as described (Saint et. al., 1986).

Primer Extension Sequencing of RNA

Adult worms of *S. japonicum* (Sorsogon Strain) were obtained by portal perfusion of infected rabbits and RNA was purified as described (Saint et. al., 1986). An oligonucleotide complementary to nucleotides 53 to 37 of the pSj1 Sj26 cDNA was extended on a single stranded DNA template isolated from M13 phage containing a complete copy of the pSj1 Sj26 cDNA. Reactions were at 20° C. for 30 minutes and contained annealed template and primer, 10 μCi each of $^{32}$PdATP and $^{32}$PdCTP, 0.05 mM dTTP, 10 mM Tris-HCl pH 8.5, 5 mM MgCl2 and 2 units of the Klenow fragment of *E. coli* DNA polymerase I. The extended primer (34 nucleotides) was excised from a 10% polyacrylamide, 7.6M urea gel and recovered by ethanol precipitation after soaking in 0.5M ammonium acetate, 5 mM EDTA, 0.1% SDS for 16 hours at 4° C. Approximately 0.5 μg of total *S. japonicum* RNA was heated at 100° C. for 1 minute with 100,000 cpm of $^{32}$P-labelled primer in the presence of 50 mM Tris-HCl pH 8.3, 0.1 mM EDTA, 10 mM DTT, 7.5 mM MgCl2, 10 mM NaCl and then incubated at 60° C. for 20 minutes. The mixture was then split into four and incubated at 42° C. for 15 minutes in reactions containing 5 units of RNAsin (BRL), 0.5 unit avian myoblastosis virus reverse transcriptase (Life Sciences Inc.), 0.1 mM each deoxynucleotide and either 0.075 mM ddATP, 0.06 mM ddCTP, 0.03 mM ddGTP or 0.15 mM ddTTP. Reaction products were separated on an 8% polyacrylamide-urea gel and detected by autoradiography.

Results

Construction of pSj10DBamI

Figure 2:
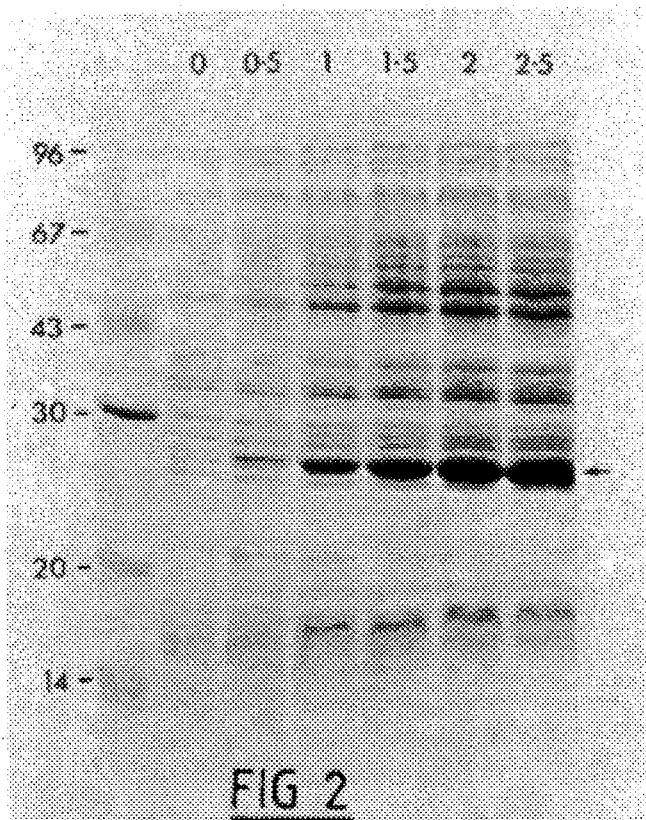
FIG. 2 shows SDS-polyacrylamide gel analysis of proteins present in cells transformed with pSj5. An overnight culture of cells was diluted 1:10 in fresh medium and incubated at 37° C. for 1 hour. IPTG was then added to 0.1 mM, and incubation was continued at 37° C. for the number of hours indicated. The size (in kDa) and position of molecular weight markers are indicated. Proteins were detected by staining with Coomassie blue.
Figure 3:
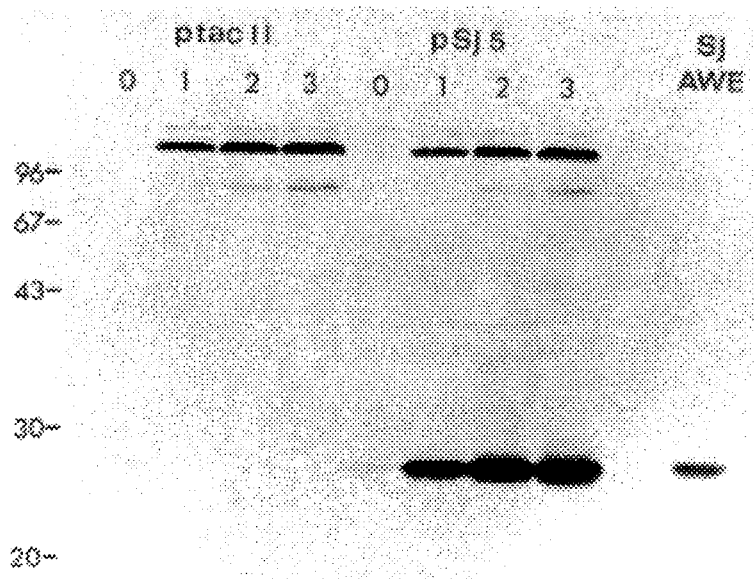
FIG. 3 shows an immunoblot of cells expressing recombinant Sj26. Samples of cells containing either ptac11 (the parental plasmid), or pSj5 were prepared as described in FIG. 2, separated on a 13% SDS-polyacrylamide gel and transferred to nitrocellulose. SjAWE is an extract of S. japonicum adult worms. The nitrocellulose was probed with a rabbit antisera prepared against purified β-galactosidase-Sj26 fusion protein (Smith et. al., 1986), followed by $I^{125}$-labelled protein A. The position and size (kDa) of molecular weight markers are indicated.
Figure 4:
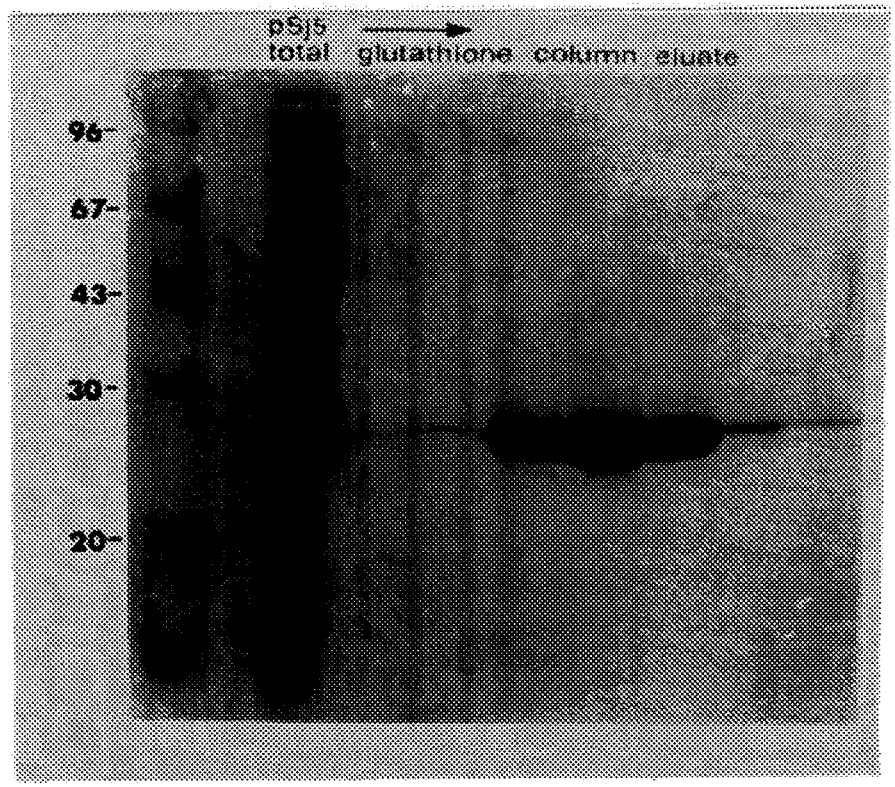
FIG. 4 illustrates the purification of recombinant Sj26. An extract of cells expressing rSj26 was applied to a glutathione-agarose column and specifically bound material eluted with free reduced-glutathione. Successive fractions of eluate or a total extract of cells were separated on a 13% SDS-polyacrylamide gel and proteins detected by staining with Coomassie blue. The position and size (kDa) of molecular weight markers are indicated.

Adult worms of the parasitic helminth *Schistosoma japonicum* contain a Mr 26,000 antigen (Sj26) that is a functional glutathione S-transferase (Mitchell et. al., 1984; Smith et. al., 1986). A plasmid was constructed (pSj5) that is expected to encode a molecule identical with native Sj26 (FIG. 1). The correct 5'-terminal structure of Sj26 (Met.Ser.Pro.Ile . . . ) was deduced from the direct sequence analysis of Sj26 mRNA purified from adult worms of *S. japonicum* (Materials and Methods) and confirmed by protein sequencing of the N-terminus of Sj26 from adult parasites (in collaboration with M.Rubira of the Joint Protein Structure Laboratory, Ludwig Institute for Cancer Research, Walter and Eliza Hall Institute of Medical Research). This plasmid directs the synthesis in *E. coli* of a Mr 26,000 molecule (recombinant Sj26, rSj26) that is indistinguisable from native Sj26 by its mobility in SDS polyacrylamide gels (FIG. 2) or its antigenicity (FIG. 3). Furthermore, this molecule is soluble, enzymatically active as a glutathione S-transferase and retains a property of many glutathione S-transferases (Simons & Vander Jagt, 1977; Harvey & Beutler, 1982) of binding to a column of immobilised glutathione (FIG. 4).

Figure 6:
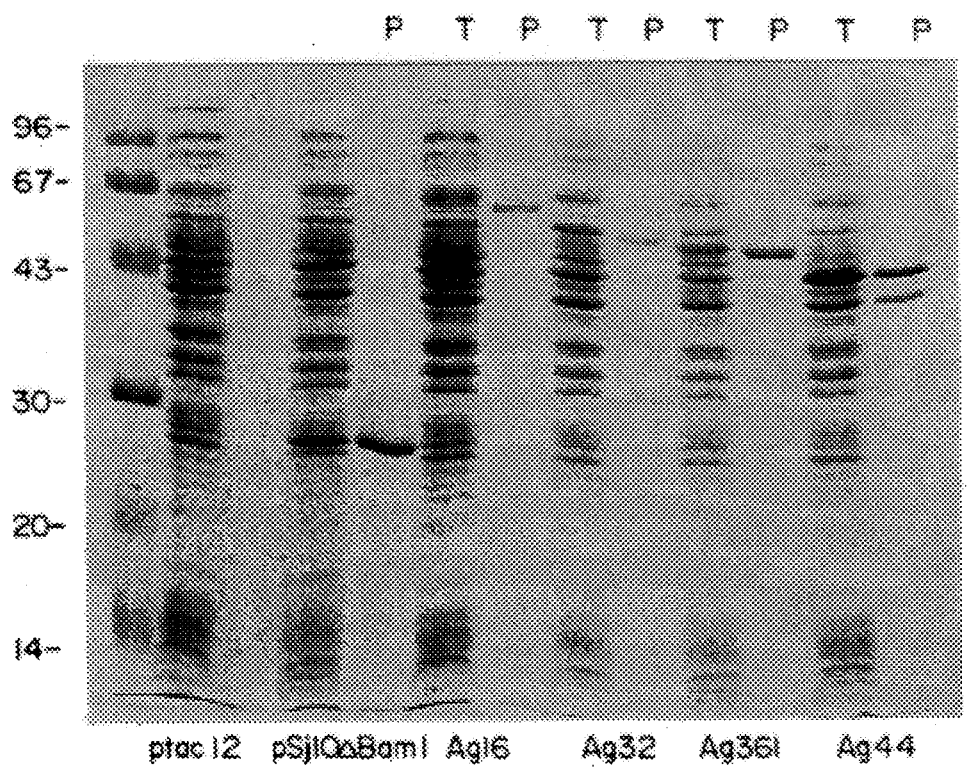
FIG. 6 shows the production and purification of Sj26-fusion proteins. Extracts of cells transformed with ptac12 (parental plasmid), pSj10DBamI or pSj10DBamI containing EcoRI fragments derived from P. falciparum antigens were separated on 13% SDS-polyacrylamide gels as either a total extract (T), or after purification on glutathione-agarose beads (P). Proteins were detected by staining with Coomassie blue. The size (kDa) and position of molecular weight markers are indicated.

A plasmid, pSj10 DBamI, was constructed that contains the complete coding sequence of Sj26 under transcriptional control of the tac promoter (Amann et. al., 1983) and followed by several unique restriction endonuclease recognition sites (Materials and Methods). Induction of cells transformed with this plasmid resulted in the synthesis of an abundant Mr 28,000 molecule (FIG. 6). The larger size of this protein is due to the destruction of the normal Sj26 termination codon in pSj10DBamI because of the introduction of a BamHI linker which results in the translation of 14 additional amino acids before an in frame termination codon is encountered. Despite these additional amino acids, the altered glutathione S-transferase is soluble and binds to glutathione (FIG. 6), suggesting that small additions to the COOH-terminus of Sj26 do not necessarily disrupt binding.

Expression of Sj26 Fusion Polypeptides

In order to test the effect of larger additions to the COOH terminus of Sj26 cDNAs corresponding to a variety of different antigens of *Plasmodium falciparum* were inserted into the unique EcoRI site of pSj10DBam1. These cDNAs were all chosen because it was known that they were in the correct reading frame for expression as Sj26-fusion proteins. The cDNAs corresponded to antigens 16 (Coppel et. al., 1983), 44 (Anders, et. al., 1984), 361 (G.Peterson, manuscript in preparation) and 32 (Cowman et. al., 1984). In each instance, transformants could be identified that expressed a novel fusion protein of Mr >28,000 that could be easily identified by Coomassie staining after electrophoresis through an SDS polyacrylamide gel (FIG. 6). Furthermore in each case the Sj26 fusion protein synthesised by these clones was soluble and could be purified from bacterial sonicates by incubation with beads incubation with beads of glutathione-agarose (FIG. 6). When the purification procedure was scaled up for 1 litre of cell suspension, about 5 mg of protein was obtained that was free of contamination as judged by Coomassie staining of polyacrylamide gels. Chromatography of lysates of untransformed cells on a glutathione column did not result in the purification of any protein. The Sj26-fusion proteins retained their antigenicity since they were recognised on Western blots by specific antisera (data not shown).

EXAMPLE 2

Materials and Methods

Construction of pGEX Vectors.

Multiple cloning sites were created in the pSj1 Sj26 cDNA (Smith et. al., 1986, 1987a) through the introduction of a BamHI linker at the unique MnlI cleavage site so that the TAA translation termination codon of Sj26 was replaced with the sequence TCGGATCC. The 5'-terminus of the pSj1 cDNA was also altered through the replacement of the 5'-terminal EcoRI-Sau96i fragment with oligonucleotides containing a BamHI cleavage site followed by the sequence CACCATGTCC and then nucleotides 12–38 of the pSj1 cDNA, so producing a BamHI fragment encoding native Sj26 (Smith et. al., 1987b). This BamHI fragment was inserted into the BamHI site of pIC19H (Marsh et. al., 1984) such that the cDNA 3'-terminus was followed by unique SmaI, EcoRI, ClaI and EcoRV cleavage sites. A blunt-ended BamHI-EcoRV fragment containing the reconstructed Sj26 cDNA was inserted into the PvuII site of ptac12ΔEco (ptac12 (Amann et. al., 1983) modified by filling in the unique EcoRI site and religation) in the correct orientation for transcription from the tac promoter. This plasmid (pSj10) was further modified through the introduction of an oligonucleotide (TGACTGACTGA) encoding stop codons in all three frames into the blunt-ended ClaI site at the cDNA 3'-terminus, while the BamHI cleavage site at the cDNA 5'-terminus was deleted by filling in using the Klenow fragment of *E. coli* DNA polymerase I.

Cells transformed with this plasmid (pSj10ΔBam7Stop7) and induced with IPTG synthesised a Mr 27,500 polypeptide but at less than 20% of the level in cells transformed with PSj5, a plasmid derived from ptac11 encoding native Sj26 (Smith et. al., 1987b). This difference in expression may be due to the increased GC content and length of the region between the tac ribosome binding site and the ATG translation initiation codon in pSj10ΔBam7Stop7 (Stormo et. al., 1982; De Boer et. al., 1983b) and so the 3'-terminus of the modified Sj26 cDNA in pSj10ΔBam7Stop7 containing the multiple cloning sites and termination codons was introduced into pSj5 as follows.

A HindIII-NdeI fragment of pSj5 encoding the tetracycline resistance gene was replaced with a 1.7 kb EcoRI fragment derived from pMC9 (Miller et. al., 1984) containing the lacI$^q$ allale and a portion of lacZ. Blunt end ligation of purified fragments after treatment with the Klenow fragment of *E. coli* DNA polymerase I produced a plasmid (p4.5) in which lacI$^q$, amp$^r$ and tac-Sj26 are all transcribed in the same direction. The EcoRI cleavage site at the 3'-terminus of the Sj26 cDNA in p4.5 was removed by filling in and religation while the EcoRI site at the cDNA 5'-6terminus was destroyed by mutagenesis as described by Mandecki (1986) using a 30-mer oligonucleotide to generate the sequence tac-GTATTC-Sj26 cDNA. A BclI fragment of this plasmid containing the 3'-terminus of lacI$^q$, the tac promoter and the 5'-portion of the Sj26 cDNA was inserted into the unique BclI site of a plasmid formed by joining a BclI-EcoRI fragment of p4.5 containing amp$^r$, ori and the 5'-portion of lacI$^q$ and a BaclI-AccI fragment of pSj10DBam7Stop7 containing the 3'-terminus of the Sj26 cDNA followed by multiple cloning sites, termination codons and nucleotides 2067–2246 of pBR322. Cleavage with BclI was on plasmid DNA grown in methylase deficient GM48 cells (Marinus., 1983) and the EcoRI and AccI terminii were blunt-ended by treatment with the Klenow fragment of *E. coli* DNA polymerase I. A transformant was identified containing a plasmid (pGEX-1) with the structure shown in FIG. 7. Oligonucleotides encoding cleavage recognition sites of thrombin or blood coagulation factor $X_a$ were inserted into the BamHI site of pGEX-1 generating plasmids (pGEX-2T and pGEX-3X) in which the unique BamHI site is frame-shifted by one or two nucleotides (FIG. 7b). Nucleotide sequences were confirmed by dideoxynucleotide sequencing of plasmid DNA (Chen & Seeburg, 1985) and except were indicated, plasmids were transformed into *E. coli* strain JM109 (Yanisch-Perron et. al., 1985). Restriction enzymes and DNA modifying enzymes were purchased from New England Biolabs and used according to the manufacturer's instructions.

P. falciparum cDNAs inserted into the pGEX vectors were a 555 bp EcoRV-EcoRI fragment and a 580 bp RsaI-EcoRI fragment of Ag63 (Bianco et. al., 1986) in SmaI-EcoRI cleaved pGEX-3X and pGEX-2T respectively, 763 bp and 1010 bp EcoRI fragments of Ag16 (Coppel et. al., 1983), and Ag361 (G.Peterson, personal communication) in EcoRI cleaved pSj10 and a 1317 bp EcoRI fragment of RESA (Favaloro et. al., 1986) in EcoRI cut pGEX-3X.

Affinity Purification of Fusion Proteins

Overnight cultures of *E. coli* transformed with parental or recombinant pGEX plasmids were diluted 1:10 in 800 ml of fresh medium and grown for 1 hour at 37° C. before adding IPTG to 0.1 mM. After a further 3–7 hours of growth cells were pelleted and resuspended in 1/50–1/100 culture volume of mouse tonicity phosphate-buffered saline (MTPBS) (150 mM NaCl, 16 mM Na$_2$HPO$_4$, 4 mM NaH$_2$PO$_4$ (pH 7.3)). Cells were lysed on ice by mild sonication and after adding Triton X-100 (BDH Chemicals) to 1%, were subjected to centrifugation at 10,000 g for 5 minutes at 4° C. The supernatant was mixed at room temperature in a 50 ml polypropylene tube on a rotating platform with 1–2 ml 50% glutathione-agarose beads (sulphur linkage, Sigma). Before use, beads were pre-swollen in MTPBS, washed twice in the same buffer and stored in MTPBS at 4° C. as a 50% solution (v/v). After absorption, beads were collected by centrifugation at 500 g for 10 seconds and washed three times with 50 ml MTPBS. Fusion protein was eluted by competition with free glutathione using 2×1 bead volume of 50 mM Tris-HCl (pH 8.0) containing 5 mM reduced glutathione (Sigma)

(final pH 7.5, freshly prepared). Absorbtion of fusion protein to the glutathione-agarose beads and subsequent elution are both complete within two minutes. Binding of fusion proteins to glutathione-agarose can be in other neutral buffers such as 50 mM Tris-HCl (pH 7.4) or MTPBS without Triton X-100, although the inclusion of detergent reduces contamination with *E. coli* proteins. Contamination can also be reduced by minimising the period during which cells are subjected to sonication. The yield of unstable fusion proteins can be increased by delaying the addition of IPTG until less than an hour before cell harvest. Yields of fusion protein were calculated from the absorbance at 280 nm using the relation 1 $OD_{280}=0.5$ mg/ml derived from protein concentration estimations (Hartree, 1972) of protein purified from cells transformed with pGEX-1 and using bovine serum albumin as a standard.

Mass screening of transformants for expression of fusion protein is conveniently carried out on 1.5 ml culture resuspended in 300 µl MTPBS. After sonication and centrifugation, the supernatant is mixed with 50µl of 50% glutathione-agarose beads, washed with 3×1 ml MTPBS and the beads boiled in 100 µl sample buffer for analysis on a 10% NaDodSO$_4$-polyacrylamide gel (Laemmli & Favre, 1973) followed by staining with 0.05% Coomassie blue.

Site-Specific Proteolysis of Fusion Proteins.

Cleavage of purified fusion proteins with thrombin was at 25° C. in elution buffer containing 150 mM NaCl, 2.5 mM CaCl$_2$ and 100 ng human thrombin (Sigma) (Eaton et. al., 1986) and 50 µg fusion protein. Cleavage with human blood coagulation factor $X_a$ was at 25° C. in elution buffer containing 100 mM NaCl, 1 mM CaCl$_2$, 500 ng human factor $X_a$ and 50 µg purified fusion protein (Nagai & Thogersen, 1984). Activation of factor X (Sigma) to factor $X_a$ was by treatment with Russell's viper venom activating enzyme (Sigma) at 37° C. for 5 minutes in a reaction containing 7 µg factor X, 75 ng activating enzyme, 8 mM Tris-HCl (pH 8.0), 70 mM NaCl and 8 mM CaCl$_2$ (Fujikawa et. al., 1972).

Results

Construction and Structure of the pGEX Vectors

The plasmid pSj5 directs the synthesis of Sj26 in *E. coli* under the control of the strong isopropyl β-D-thiogalactopyranoside (IPTG)-inducible taC promoter (Smith et. al., 1987b). Through a series of manipulations pSj5 was modified so that foreign polypeptides could be expressed as fusions with the COOH-terminus of Sj26. The resulting plasmid (pGEX-1) (FIG. 7) contains (a) the tac promoter (Amann et. al., 1983; De Boer et. al., 1983a) followed by the complete coding sequence of Sj26 (Smith et. al., 1986, 1987a) in which the normal termination codon is replaced by a polylinker containing unique recognition sites for the restriction endonucleases BamHI, SmaI and EcoRI and followed by TGA translation termination codons in all three reading frames (FIG. 7b), (b) the β-lactamase gene conferring resistance to ampicillin, (c) an origin of replication and (d) a fragment of the lac operon containing the overexpressed lacI$^q$ allele of the lac repressor and part of lacZ. Two derivatives of pGEX-1 were constructed (pGEX-2T and pGEX-3X, FIG. 7b) in which the reading frame at the multiple cloning site is shifted by either one or two nucleotides through the introduction of oligonucleotides encoding the cleavage recognition sequences of the site-specific proteases thrombin (pGEX-2T) or blood coagulation factor $X_a$ (pGEX-3X).

Figure 8A:
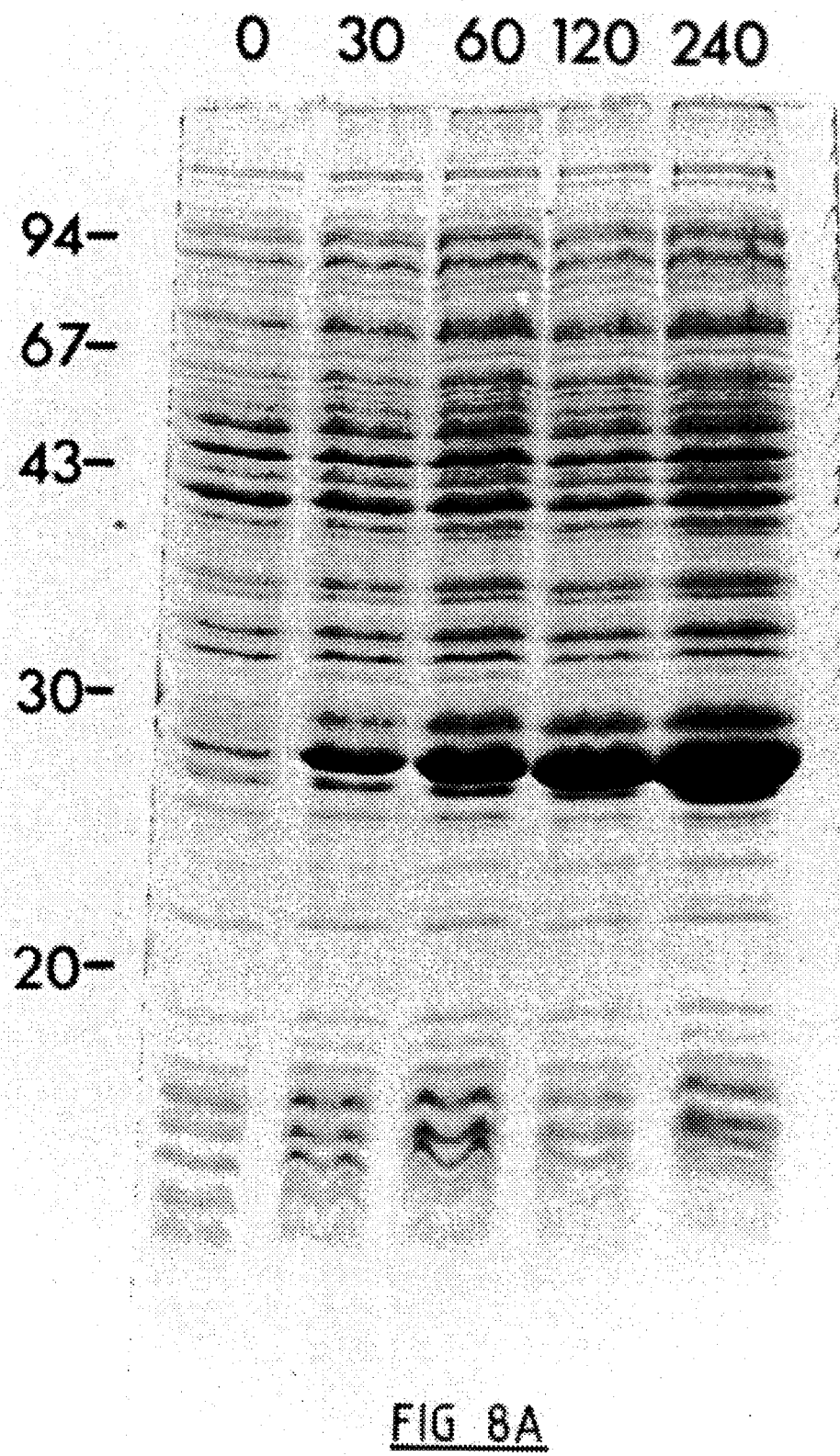
FIG. 8 shows the expression and purification of glutathione S-transferase in cells transformed with pGEX-1.
Figure 8B:
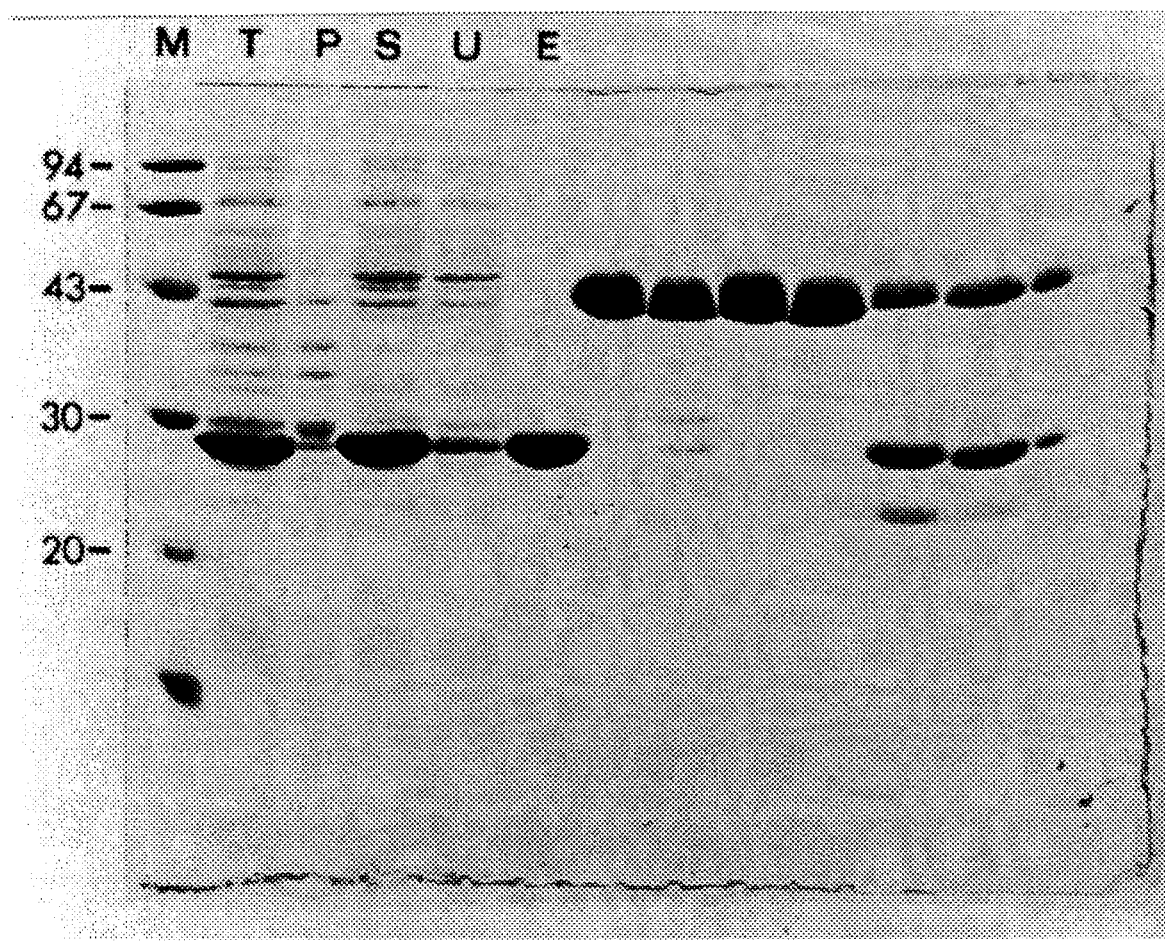

Induction of the tac promoter with IPTG in cells transformed with pGEX-1 results in the synthesis of a Mr 27,500 polypeptide consisting of Sj26 with ten additional aminoacid residues at its COOH-terminus (FIG. 8a). Despite its abundance, the Mr 27,500 polypeptide does not form insoluble inclusion bodies and remains in the supernatant of cells lysed by sonication and subjected to centrifugation at 10,000 g for 5 minutes (FIG. 8b). Furthermore, the COOH-terminal extension to Sj26 does not affect binding to glutathione-agarose and so affinity chromatography of cell extracts results in the efficient purification of the Mr 27,500 molecule with yields of at least 15 mg/litre of culture and in the absence of detectable contamination with *E. coli* proteins (FIG. 8b). Similar properties are observed for the modified Sj26 polypeptides encoded by pGEX-2T and pGEX-3X that both contain 14 additional residues at the COOH-terminus. In the absence of inducer, the plasmid encoded lacI$^q$ allele is efficient in repressing transcription from the tac promoter (FIG. 8a), even in *E. coli* strains such as C600 or GM48 (Marinus, 1973) that carry a wildtype lacI allele (unpublished data).

Expression and Purification of *Plasmodium falciparum* Antigens

In order to test the generality of the pGEX vectors as a system for the expression and purification of foreign polypeptides, cDNAs corresponding to several different antigens of *Plasmodium falciparum*, the causative agent of falciparum malaria, were inserted into the multiple cloning site of the appropriate pGEX vector. The cDNAs chosen encode portions of two different antigens (Ag63, Ag361) both related to heat shock protein 70 (Bianco et. al., 1986; Peterson et. al., 1987), and two antigens containing tandemly repeated peptides (Ag16, EcoRI-RESA)(Coppel et. al., 1983; Favaloro et. al., 1986). In each case synthesis of an abundant glutathione S-transferase-fusion protein was observed and these fusion proteins could be purified by affinity chromatography of cell extracts on immobilised glutathione with yields of between 1.6 and 5 mg/litre of culture (FIG. 9). Other polypeptides that have been successfully expressed and purified using the pGEX vectors include 8 other *P. falciparum* antigens, ten different antigens of the parasitic tapeworms *Taenia ovis* and *T. taeniaformis*, and murine interleukin-4 and granulocyte-macrophage colony stimulating factor (unpublished data).

Protease Cleavage of Purified Fusion Proteins

The utility of the pGEX vectors for the production of foreign polypeptides in *E. coli* can be increased if following purification, the glutathione S-transferase carrier can be removed from fusion proteins by cleavage with site-specific proteases. This approach has proved successful for fusion proteins containing the recognition site of blood coagulation factor $X_a$ (Nagai & Thogersen, 1984) or collagenase (Germino & Bastia, 1984), but has sometimes been ineffective (Allen et. al., 1985).

Figure 10A:
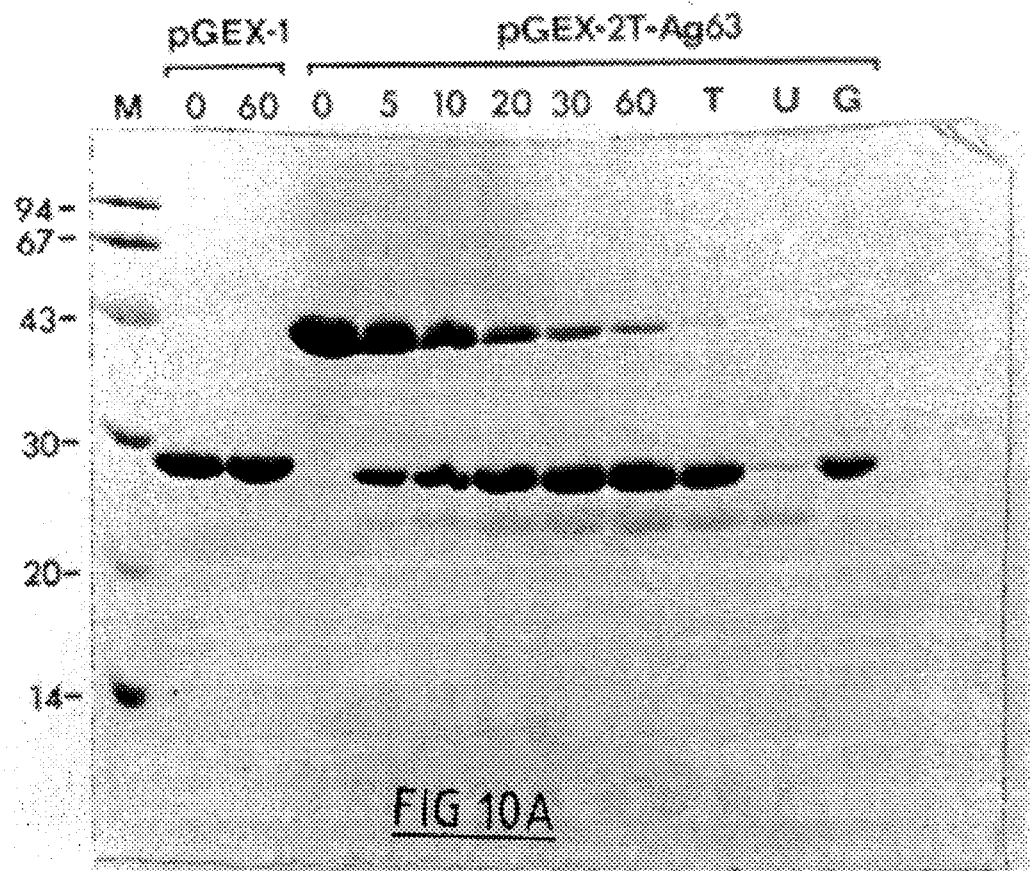
Figure 10B:
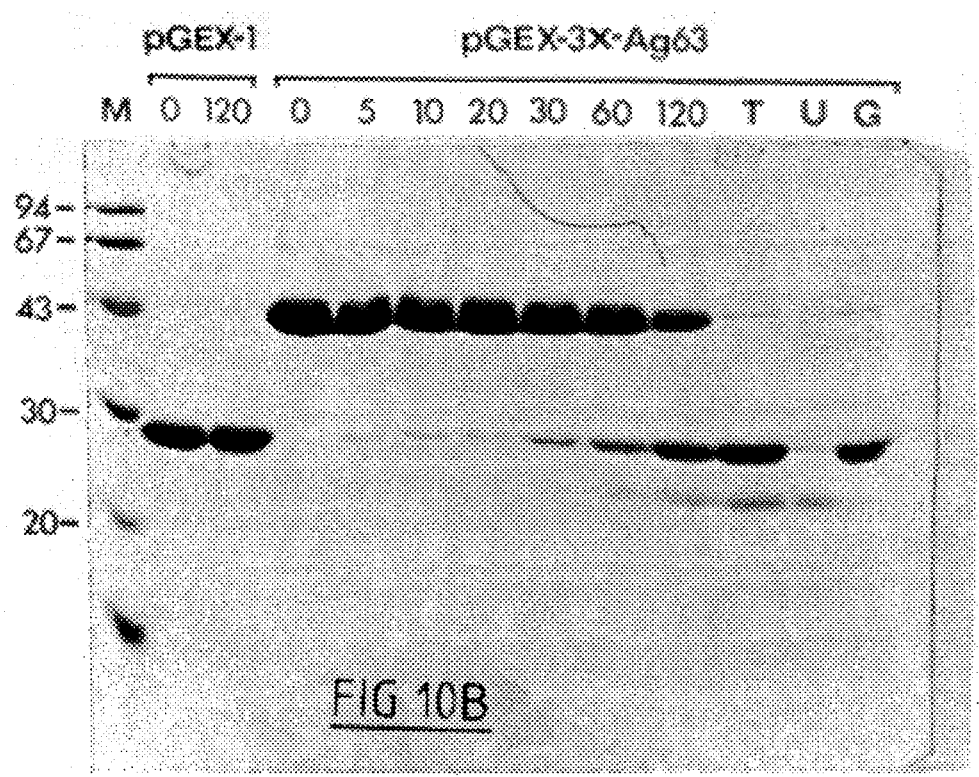

Oligonucleotides encoding the cleavage recognition site of thrombin (Chang, 1985) or blood coagulation factor $X_a$ (Nagai & Thogersen, 1984) were introduced immediately 5' to the multiple cloning site of pGEX-1 generating the plasmids pGEX-2T and pGEX-3X respectively (FIG. 7b). Insertion of a 580 base-pair (bp) RsaI-EcoRI fragment of the Ag63 cDNA (Bianco et. al., 1986) into the SmaI-EcoRI sites of pGEX-2T resulted in the expression of a Mr 43,000 fusion protein that could be purified on glutathione-agarose (FIG. 10a). Incubation of this protein with thrombin led to the production of two fragments, one the glutathione S-transferase carrier, and the other a Mr 22,500 portion of Ag63 (FIG. 10a). Efficient cleavage occurred within 30 minutes and at an enzyme to substrate ratio of 1:500. A small proportion of fusion protein was resistant to cleavage even after incubation for two hours with a ten-fold higher concentration of enzyme. Similarly, expression of a 555 bp EcoRV-EcoRI fragment of Ag63 using the pGEX-3X vector resulted in the synthesis of a Mr 43,000 fusion protein that was cleaved into two fragments by blood coagulation factor $X_a$ (FIG. 10b). Cleavage with factor $X_a$ was slower and less efficient than with thrombin, possibly due to inefficient activation of factor X. Three other pGEX-2T fusion and one additional pGEX-3X fusion have been tested for susceptibility to cleavage by the appropriate protease and in each case efficient cleavage was observed (unpublished data). Neither of the proteases cleave the glutathione S-transferase carrier and so after proteolysis both the carrier and any uncleaved fusion protein can be removed from the cleavage reaction by absorption on glutathione-agarose leaving only the purified polypeptide product (FIG. 10).

REFERENCES

1. Abrahamsen, L., Moks, T., Nilsson, B. and Uhlen, M. (1986), *Nucl.Acids Res.* 14, 7487–7500.
2. Allen, G., Paynter, C. A. and Winther, M. D. (1985) *J.Cell.Sci.Suppl.* 3, 29–38.
3. Amann, E., Brosius, J. and Ptashne, M. (1983) *Gene* 25, 167–178.
4. Anders, R. F., Coppel, R. L., Brown, G. V., Saint, R. B., Cowman, A. F., Lingelbach, K. R., Mitchell, G. F. and Kemp, D. J. (1984) *Mol. Biol. Med.* 2: 177–191.
5. Balloul, J. M., Sondermeyér, P., Dreyer, D., Capron, M., Grzych, J. M., Pierce, R. J., Carvallo, D., Lecoq, J. P. and Capron, A. (1987), *Nature* 326, 149–153.
6. Bianco, A. E., Favaloro, J. M., Burkot, T. R., Culvenor, J. G., Crewther, P. E., Brown, G. V., Anders, R. F., Coppel, R. L., and Kemp, D. J. (1986), *Proc.Natl.Acad.Sci.USA* 83, 8713–8717.
7. Chang, J-Y. (1985), *Eur.J.Biochem.* 151, 217–224.
8. Chen, E. Y. and Seeburg, P. H. (1985) *DNA* 4, 165–170.
9. Cheng, Y-S. E., Kwoh, D. Y., Kwoh, T. J., Soltvedt, B. C. and Zipser, D. (1981), *Gene* 14, 121–130.
10. Coppel, R. L., Cowman, A. F., Lingelbach, K. R., Brown, G. V., Saint, R. B., Kemp, D. J. and Anders, R. F. (1983), *Nature* 306, 751–756.
11. Cowman, A. F., Coppel, R. L., Saint, R. B., Favaloro, J. M., Crewther, P. E., Stahl, H. D., Bianco, A. E., Brown, G. V., Anderes, R. F. and Kemp, D. J., (1984) *Mol.Biol.Med.* 2: 207–221.
12. Crewther, P. E., Bianco, A. E., Brown, G. V., Coppel, R. L., Stahl, H. -D., Kemp, D. J. and Anders, R. F. (1986) *Methods* 86: 257–264.
13. Davern, K. M., Tiu, W. U., Morahan, G., Wright, M. D., Garcia, E. G. and Mitchell, G. F. (1987), *Immunol.Cell.Bioil.* (in press).
14. De Boer, H. A., Comstock, L. J. and Vasser, M. (1983a), *Proc.Natl.Acad.Sci.USA* 80, 21–25.
15. De Boer, H.A., Comstock, L. J. and Vasser, M. (1983b) *DNA* 2, 231–235.
16. Eaton, D., Rodriguez, H. and Vehar, G. A. (1986), *Biochemistry* 25, 505–512.
17. Favaloro, J. M., Coppel, R. L., Corcoran, L. M., Foote, S. J., Brown, G. V., Anders, R. F. and Kemp, D. J. (1986), *Nucl.Acids Res.* 14, 8265–8277.
18. Fujikawa, K., Legaz, M. E. and Davie, E. W. (1972), *Biochemistry* 11, 4892–4899.
19. Germino, J. and Bastia, D. (1984), *Proc.Natl.Acad.Sci.USA,* 81, 4692–4696.
20. Germino, J., Gray, J. G., Charbonneau, H., Vanaman, T. and Bastia, D. (1983), *Proc.Natl.Sci.USA* 80, 6848–6852.
21. Gray, M. R., Colot, H. V., Guarente, L. and Rosbash, M. (1982), *Proc.Natl.Acad.Sci.USA* 79, 6598–6602.
22. Haffey, M. L., Lehman, D. and Boger, J. (1987), *DNA* 6, 565.
23. Harris, T. J. R. (1983). In Williamson R. (ed), *Genetic Engineering,* Academic Press, London, Vol. 4 128–175.
24. Hartree, E. F. (1972) *Anal.Biochem.* 48, 422–427.
25. Harvey, J. W. and Beutler, E. (1982). *Blood* 60: 1227–1230.
26. Itakura, K., Hirose, T., Crea, R., Riggs, A. D., Heyneker, H. L., Bolivar, F. and Boyer, H. W. (1977), *Science* 198, 1056–1063.
27. Kato, C., Kobayashi, T., Kudo, T., Furusato, T., Murakami, Y., Tanaka, T., Baba, H., Oishi, T., Ohtsuka, E., Ikehara, M., Yanagida, T., Kato, H., Moriyama, S. and Horikoshi, K. (1987), *Gene* 54, 197–202.
28. Koenen, M., Ruther, U. and Muller-Hill, B. (1982), *EMBO. J,* 1, 509–512.
29. Kleid, D. G., Yansura, D., Small, B., Dowbenko, D., Moore, D. M., Grubman, M. J., McKercher, P. D., Morgan, D. O., Robertson, B. H. and Bachrach, H. C. (1981), *Science* 214, 1125–1129.
30. Laemmli, U. K. and Favre, M. (1973), *J. Mol. Biol.* 80, 575–599.
31. Langford, C. J., Edwards, S. J., Smith, G. L., Mitchell, G. F., Moss, B., Kemp, D. J. and Anders, R. F. (1986) *Mol.Cell.Biol.* 6: 3191–3199.
32. Lowenadler, B., Nilsson, B., Abrahmsen, L., Moks, T., Ljunggvist, L., Holmgren, E., Paleus, S., Josephson, S., Philipson, L. and Uhlen, M. (1986), *EMBO J.* 5, 2393–2398.
33. McIntyre, P., Coppel, R. L., Smith, D. B., Stahl, H. D., Corcoran, L. M., Langford, C. J., Favaloro, J. M., Crewther, P. E., Brown, G. V., Mitchell, G. F., Anderson, R. F. and Kemp, D. J. (1987) *Int.J.Parasitol.* 17, 59–67.
34. Mandecki, W. (1986), *Proc.Natl.Acad. Sci.USA* 83, 7177–7181.
35. Maniatis, T., Fritsch, E. F. and Sambrook, J. "Molecular cloning: a laboratory manual" Cold Spring Harbor Laboratory, 1982.
36. Mannervik, B. (1985), *Adv.Enzymol.* 57, 357–417.
37. Marinus, M. G. (1973), *Molec.Gen.Genet.* 127, 47–55.
38. Marsh, J. L., Erfle, M. and Wykes, E. J. (1984), *Gene* 32, 481–485.
39. Marston, A. O. (1986), *Biochem, J* 240, 1–12.
40. Miller, J. H., Lebkowski, J. S., Greisen, K. S. and Calos, M. P. (1984), *EMBO, J.* 3, 3117–3121.
41. Mitchell, G. F., Cruise, K. M., Garcia, E. G. and Tiu, W. U. (1984) *J. Parasitol.* 70: 983–985.
42. Nagai, K. and Thogersen, H. C. (1984), *Nature* 309, 810–812.
43. Nilsson, B., Abrahmsen, L. and Uhlen, M. (1985), *EMBO J.* 4, 1075–1080.
44. Peterson, M. G., Crewther, P. E., Thompson, J. K., Corcoran, L. M., Coppel, R. L., Brown, G. V., Anders, R. F. and Kemp, D. J. (1987) *DNA* (in press).
45. Ruther, U. and Muller-Hill, B. (1983), *EMBO J.* 2, 1791–1794.
46. Saint, R. B., Beall, J. A., Grumont, R. J., Mitchell, G. F. and Garcia, E. G. (1986) *Mol.Biochem.Parasitol.* 18: 333–342.
47. Sassenfeld, H. M., and Brewer, S. J. (1984), *Bio.Technology* 2, 76–81.
48. Schoemaker, J. M., Brasnett, A. H. and Marston, A. O. (1985), *EMBO. J.* 4, 775–780.
49. Simons, P. C. and Vander Jagt, D. L. (1977), *Anal.Biochem.* 82, 334–341.

50. Simons, P. C. and Vander Jagt, D. L. (1981), *Methods Enzymol.* 77, 235–237.
51. Smith, D. B., Davern, K. M., Board, P. G., Tiu, W. U., Garcia, E. G. and Mitchell, G. F. (1986), *Proc.Natl.Acad.Sci.USA* 83, 8703–8707.
52. Smith, D. B., Davern, K. M., Board, P. G., Tiu, W. U., Garcia, E. G. and Mitchell, G. F. (1987a), *Proc.Natl.Acad. Sci.USA* 84, 6541.
53. Smith, D. B., Rubira, M. R., Simpson, R. J., Davern, K. M., Tiu, W. U., Board, P. G. and Mitchell, G. F. (1987b), *Mol.Biochem.Parasitol.* (in press).
54. Stanley, K. K. and Luzio, J. P. (1984), *EMBO. J.* 3, 1429–1434.
55. Stormo, G. D., Schneider, T. D. and Gold, L. M. (1982), *Nucl.Acids.Res.* 10, 2971–2996.
56. Uhlen, M., Nilsson, B., Guss, B., Lindberg, M., Gatenbeck, S. and Philipson, L. (1983), *Gene* 23, 369–378.
57. Ullmann, A. (1984), *Gene* 29, 27–31.
58. Yanisch-Perron, C., Vieira, J. and Messing, J. (1985), *Gene* 33, 103–119.
59. Young, R. A. and Davis, R. W. (1983), *Proc.Natl.Acad, Sci.USA*, 80, 1194–1198.

I claim:

1. A recombinant DNA molecule comprising a nucleotide sequence which codes for a fusion protein wherein said fusion protein comprises glutathione-S-transferase and a second protein or peptide fused directly or indirectly with the COOH-terminus of glutathione-S-transferase, and wherein said fusion protein is capable of binding to glutathione.

2. The recombinant DNA molecule according to claim 1, wherein said glutathione-S-transferase is the 26kDa glutathione-S-transferase of *Schistosoma japonicum*.

3. The recombinant DNA molecule according to claim 1 wherein said second protein or peptide is fused to said glutathione-S-transferase through a cleavable link.

4. The recombinant DNA molecule according to claim 3, wherein said cleavable link is cleavable by a site specific protease.

5. The recombinant DNA molecule according to claim 4, wherein said clearable link is cleavable by thrombin, blood coagulation factor $X_a$ or renin.

6. The recombinant DNA molecule of claim 1 wherein said glutathione-S-transferase is a mammalian glutathione-S-transferase.

7. An expression vector comprising the recombinant DNA molecule of any one of claims 1, 2–5 and 6.

8. A host cell comprising the expression vector of claim 7.

9. The host cell of claim 8 wherein said host cell is a bacterial cell.

10. The host cell according to claim 9 which is *E. coli*.

11. An expression vector comprising, in the 5' to 3' direction, a promoter, a nucleotide sequence encoding glutathione-S-transferase and a nucleotide sequence comprising at least one restriction endonuclease recognition site.

12. The expression vector according to claim 11, wherein said glutathione-S-transferase is the 26kDa glutathione-S-transferase of *Schistosoma japonicum*.

13. The expression vector according to claim 11, which comprises a plasmid selected from the group consisting of pGEX-1, pSj10 DBamI and pSj10 DBam7Stop7.

14. An expression vector comprising, in the 5' to 3' direction, a promoter, a nucleotide sequence encoding glutathione-S-transferase, a nucleotide sequence encoding a clearable link and a nucleotide sequence comprising at least one restriction endonuclease recognition site.

15. The expression vector according to claim 14, wherein said cleavable link is cleavable by a site specific protease.

16. The expression vector according to claim 14 which is pGEX-2T or pGEX-3X.

17. The plasmid pGEX-1.

18. The plasmid pGEX-2T.

19. The plasmid pGEX-3X.

20. A method of producing a fusion protein comprising glutathione-S-transferase and a second protein or peptide fused directly or indirectly with the COOH-terminus of glutathione-S-transferase which comprises:

(a) transforming a host cell with an expression vector comprising a promoter operatively linked to a nucleotide sequence which codes for a fusion protein wherein said fusion protein comprises glutathione-S-transferase and a second protein or peptide fused directly or indirectly with the COOH-terminus of glutathione-S-transferase and wherein said fusion protein is capable of binding to glutathione;

(b) culturing said host cell under conditions such that said fusion protein is expressed in recoverable quantity;

(c) lysing said host cell; and (d) purifying said fusion protein by glutathione-affinity chromatography.

21. A method of producing a protein or peptide which comprises:

(a) transforming a host cell with an expression vector comprising a promoter operatively linked to a nucleotide sequence which codes for a fusion protein wherein said fusion protein comprises glutathione-S-transferase and a second protein or peptide fused with the COOH-terminus of glutathione-S-transferase through a cleavable link wherein said fusion protein is capable of binding to glutathione;

(b) culturing said host cell under conditions such that said fusion protein is expressed in recoverable quantity;

(c) lysing said host cell;

(d) purifying said fusion protein by glutathione-affinity chromatography;

(e) cleaving said protein or said peptide from said glutathione-S-transferase; and (f) isolating said protein or said peptide.

22. A fusion protein comprising glutathione-S-transferase and a second protein or peptide fused directly or indirectly with the COOH-terminus of said glutathione-S-transferase wherein said fusion protein is capable of binding to glutathione.

23. A fusion protein comprising from amino to carboxyl terminus, glutathione-S-transferase, a cleavable linker and a second protein or peptide wherein said fusion protein is capable of binding to glutathione.

24. The fusion protein of claim 23 wherein said cleavable linker is cleavable by a site-specific protease.

25. The fusion protein of claim 24 wherein said protease is selected from the group consisting of thrombin, blood coagulation Factor Xa and renin.

* * * * *

UNITED STATES PATENT AND TRADEMARK OFFICE
CERTIFICATE OF CORRECTION

PATENT NO. : 5,654,176
DATED : August 5, 1997
INVENTOR(S) : Donald B. Smith

It is certified that error appears in the above-identified patent and that said Letters Patent is hereby corrected as shown below:

Column 7, line 3: "ptac11 1" should read --ptac11--

Column 10, line 10: "5'-6terminus" should read --5'-terminus--

Signed and Sealed this

Second Day of March, 1999

Attest:

Q. TODD DICKINSON

*Attesting Officer*  *Acting Commissioner of Patents and Trademarks*